US011324962B2

(12) United States Patent
Sandstrom

(10) Patent No.: US 11,324,962 B2
(45) Date of Patent: May 10, 2022

(54) MAGNETIC FIELD ENHANCEMENT OF CHEMOTHERAPY FOR TUMOR TREATMENT

(71) Applicant: Robert E. Sandstrom, Longview, WA (US)

(72) Inventor: Robert E. Sandstrom, Longview, WA (US)

(*) Notice: Subject to any disclaimer, the term of this patent is extended or adjusted under 35 U.S.C. 154(b) by 360 days.

(21) Appl. No.: 16/283,428

(22) Filed: Feb. 22, 2019

(65) Prior Publication Data
US 2019/0255345 A1 Aug. 22, 2019

Related U.S. Application Data

(60) Provisional application No. 62/633,794, filed on Feb. 22, 2018.

(51) Int. Cl.
*A61N 2/00* (2006.01)
*G16H 20/30* (2018.01)
*G16H 20/10* (2018.01)
*A61N 2/02* (2006.01)

(52) U.S. Cl.
CPC ............ *A61N 2/002* (2013.01); *A61N 2/004* (2013.01); *G16H 20/30* (2018.01); *A61N 2/02* (2013.01); *G16H 20/10* (2018.01)

(58) Field of Classification Search
CPC .................................. A61N 2/02; A61N 2/00
See application file for complete search history.

(56) References Cited

U.S. PATENT DOCUMENTS

| 5,211,622 | A | * | 5/1993 | Liboff | ...................... | A61N 2/02 600/14 |
|---|---|---|---|---|---|---|
| 6,679,827 | B2 | | 1/2004 | Sandstrom | | |
| 6,749,596 | B2 | | 6/2004 | Gray | | |
| 6,926,659 | B1 | | 8/2005 | Sandstrom | | |
| 7,731,648 | B2 | | 6/2010 | Ivkov | | |
| 8,888,674 | B2 | | 11/2014 | Shapiro | | |
| 8,932,636 | B2 | | 1/2015 | Peyman | | |
| 9,616,245 | B2 | | 4/2017 | Kumar | | |
| 9,687,668 | B2 | | 6/2017 | McKenna | | |

(Continued)

FOREIGN PATENT DOCUMENTS

| JP | 2007521109 A | 8/2007 |
|---|---|---|
| WO | 2017173352 A1 | 10/2017 |
| WO | 2018172863 A1 | 9/2018 |

OTHER PUBLICATIONS

Verdom et al. "The static Magnetic Field Remotely Boosts the Efficiency of Doxorubicin through Modulating ROS Behaviors" Scientific Reports 8:9 90 (Year: 2018).*

(Continued)

*Primary Examiner* — Kaylee R Wilson
(74) *Attorney, Agent, or Firm* — Timothy E. Siegel Patent Law, PLLC; Timothy E. Siegel

(57) ABSTRACT

A therapeutic magnetic field device, having a magnetic field generator; a magnetic field sensor; and a data entry panel, permitting a user to input time periods and electromagnetic field strengths, for an electromagnetic field production regime. The device also includes a data processor including non-transitory computer readable memory, adapted to control the magnetic field generator to output a magnetic field in accordance with data received from the data entry panel.

10 Claims, 1 Drawing Sheet

(56) References Cited

U.S. PATENT DOCUMENTS 9,789,328 B2 10/2017 Sandstrom
2002/0051751 A1 5/2002 Mills
2013/0323165 A1 12/2013 Campbell

OTHER PUBLICATIONS

Chakkalakal et al. "Magnetic field induced inhibition of human osteosarcoma cells treated with Adriamycin" Cancer Biochemistry Biophysics, vol. 17, pp. 89-98 (Year: 1999).*
Po-Chin Liang et al, Doxorubicin-modified magnetic nanoparticles as a drug delivery system for magnetic resonance imaging-monitoring magnet-enhancing tumor chemotherapy, International Journal of Nanomedicine, May 12, 2016.

* cited by examiner

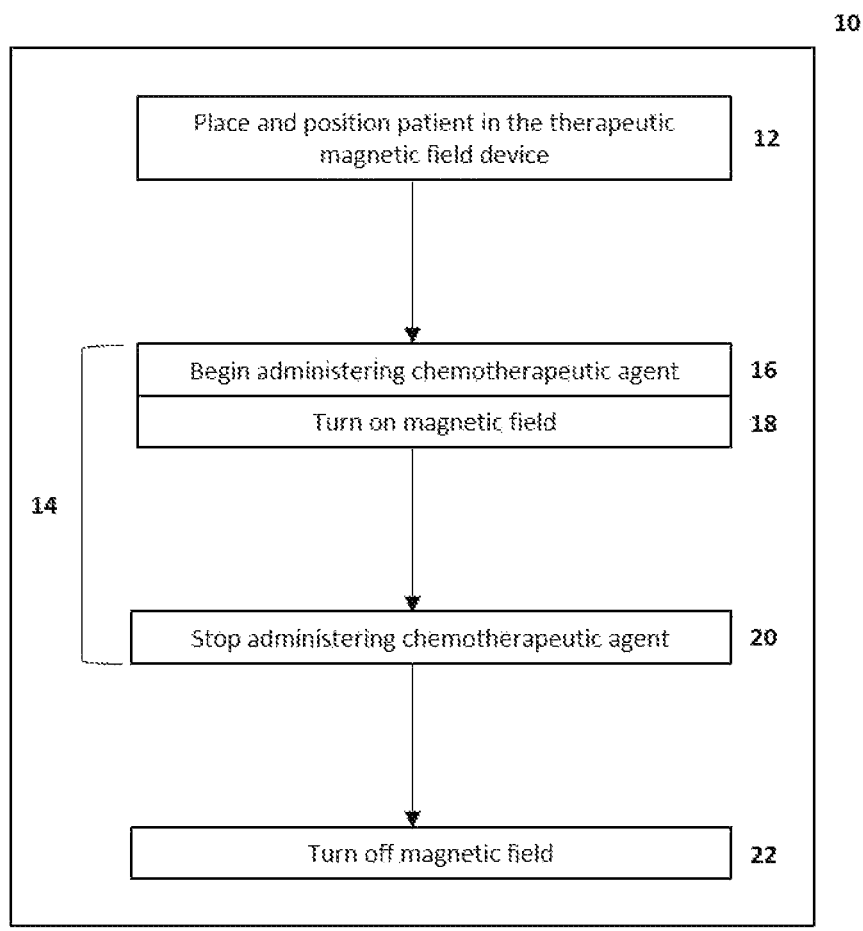

MAGNETIC FIELD ENHANCEMENT OF CHEMOTHERAPY FOR TUMOR TREATMENT

BACKGROUND

A number of cancer chemotherapy drugs act through free radical intermediates. Current agents which are thought to act through free radical intermediates include bleomycin, doxorubicin, cyclohexamide, and vincristine. Other agents acting through free radical intermediates are under development. In some instances, free radicals may be involved in signaling pathways or metabolic steps as secondary actors in the course of cancer chemotherapy.

Free radicals produced from a parent compound through chemical steps which include ionization, homolytic fission, enzymatic action, or other metabolic processes. Free radicals may be ionic or nonionic and are characterized by the presence of an unpaired electron in the outer orbital shell of the parent molecule. Entities with an unpaired electron are subject to magnetic field effects. The radical will precess in a magnetic field of selective and specific field strength in a manner comparable to classic paramagnetic and magnetic entities as defined by Larmor precession mechanics.

Free radicals, once generated from a parent compound, may recombine with the electron removed from the chemotherapeutic compound. It is the non-recombinant free radical which is biologically active. Free radicals may directly damage cell structures, damage DNA or RNA or induce apoptosis through the induction of apoptotic pathways resulting in cell death.

Variables which influence recombination rates include alternate chemical reactions, temperature, viscosity and the quantum state of the free radical. The quantum state of the free radical is defined by the applicable Schrödinger equation and the wave function (eigenfunction). The eigenfunction is defined by a set of four quantum numbers: n—the principal quantum number, l—the orbital quantum number, $m_l$—the magnetic quantum number, and $m_s$—the spin quantum number. An unpaired orbital electron can assume one of two values, $+\frac{1}{2}$ or $-\frac{1}{2}$, conventionally referred to as up (+) and down (−) spins.

The unpaired electron is subject to magnetic field effects. A magnetic field will induce spin phase transitions between a singlet states with antiparallel spin orientation to non-antiparallel spin orientation in the triplet state. A specific magnetic field strength characterizes the precession effect. The effect is specifically magnetic and can be induced by a static magnetic field of specific field strength or by a magnetic field created by an induction coil. Generally speaking the specific field strength will lie between 10 and 500 Gauss; magnetic field strengths below and above the optimum field strength will prove ineffective. The upper field strength will specifically be limited by the Zeeman energy level. Given the appropriate magnetic field and precession of the free radical, the theoretical distribution of the singlet to triplet state will be 25% singlet and 75% triplet. Non-quantum factors as mentioned may effect that distribution but increases in escape radical reactivity of 30-40% have been experimentally demonstrated. A 30-40% increase in chemotherapy effect can result in higher tumor cell kill, lower effective administered doses, and given the potential to target the magnetic field to specific anatomic sites the ability to limit bystander cell damage.

U.S. Pat. Nos. 6,679,827 and 6,926,659 disclose a method for enhancing tumor treatment by creating a magnetic field that treats a tumor. Chemotherapy which is usually not targeted and administered systemically by intravenous or oral routes presents unique problems not addressed by the referenced patents. Each of the chemotherapeutic agents has a specific quantum state which dictates the requisite magnetic field strength. Each of the compounds has a specific organ distribution and importantly a specific half-life which may be altered by concurrent health conditions or disease and age. If targetable in some formulations, then an ability to focus the magnetic field may be useful. An electrical field is not specific to the precession effect. Furthermore, an electrical field suffers from poor permittivity in tissues and because of tissue resistance if employed may induce significant thermal damage limiting its application to tissue sites. The method postulates no specific effect on mitotic structures beyond the generalized damage induced by free radicals in tissue.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a therapeutic magnetic field device, having a magnetic field generator; a magnetic field sensor; and a data entry panel, permitting a user to input time periods and electromagnetic field strengths, for an electromagnetic field production regime. The device also includes a data processor including non-transitory computer readable memory, adapted to control the magnetic field generator to output a magnetic field in accordance with data received from the data entry panel.

In a second separate aspect, the present invention may take the form of a method for enhancing the chemotherapeutic treatment of cancer tumors, including the steps of placing the patient into the therapeutic magnetic field device, having a magnetic field generator; a magnetic field sensor; a data entry panel, permitting a user to input time periods and electromagnetic field strengths, for an electromagnetic field production regime; and a data processor including non-transitory computer readable memory, adapted to control the magnetic field generator to output a magnetic field in accordance with data received from the data entry panel. In the method, a chemotherapeutic agent is administered to a patient, the first chemotherapeutic agent having a biological half-life, and an optimal field strength that is dictated by a specific quantum state of the chemotherapeutic agent. During administration of the chemotherapeutic agent, the patient is exposed to a magnetic field having the optimal field strength of the chemotherapeutic agent during administration of the chemotherapeutic agent. Finally, after administration of the chemotherapeutic agent, the patient is exposed to the magnetic field having the optimal field strength of the chemotherapeutic agent for a period up to five-times the biological half-life of the chemotherapeutic agent.

In a third separate aspect, the present invention may take the form of a method for enhancing the chemotherapeutic treatment of cancer tumors, comprising the steps of placing the patient into the therapeutic magnetic field device, that has a magnetic field generator; a magnetic field sensor; a data entry panel, permitting a user to input time periods and electromagnetic field strengths, for an electromagnetic field production regime; and a data processor including non-transitory computer readable memory, adapted to control the magnetic field generator to output a magnetic field in accordance with data received from the data entry panel. A chemotherapeutic cocktail is administered to a patient, wherein the chemotherapeutic cocktail comprises a first chemotherapeutic agent, the first chemotherapeutic agent having a biological half-life, and an optimal field strength that is dictated by a specific quantum state of the first chemotherapeutic agent. During administration of the chemotherapeutic cocktail, the patient is exposed to a magnetic field. Finally, after administration of the chemotherapeutic cocktail, continuing to expose the patient to the magnetic field for a duration up to five-times the biological half-life of the first chemotherapeutic agent.

Further, this submission postulates a method which employs ferrimagnets, Helmholtz coils, or an array of such magnetic sources which are employed during the administration of a chemotherapeutic agent. The magnetic sources are arrayed to provide a uniform selective magnetic field which encompasses the patient. The field is employed during the course of administration of the agent and for an extended period after completion of the administration of the drug for a period that extends up to five times the patient specific biological half-life of the drug but not generally less than one hour after completion of the administration schedule.

Where useful and feasible magnetic shielding and positioning the source magnets will be employed to target specific tissue sites while sparing non-tumor sites. In selective situations a magnetic field of determinate field strength may be created employing portable devices or devices worn or carried by the patient.

In addition to the exemplary aspects and embodiments described above, further aspects and embodiments will become apparent by reference to the drawings and by study of the following detailed descriptions.

BRIEF DESCRIPTION OF THE DRAWING

Exemplary embodiments are illustrated in referenced drawings It is intended that the embodiments and figure disclosed herein are to be considered illustrative rather than restrictive.

FIG. 1 is a flow chart showing the overall method steps implemented in accord with one exemplary embodiment.

DETAILED DESCRIPTION OF THE PREFERRED EMBODIMENTS

Referring to FIG. 1, the overall method steps implemented in accordance with preferred embodiments of the present invention are described. At the start of a chemotherapy session 10, a patient is placed in a therapeutic magnetic field device and positioned comfortably for the treatment procedure (action block 12). Typically, a patient is positioned in a manner such that the tumor sites can be optimally exposed to a magnetic field generated by the therapeutic magnetic field device; the determination of appropriate positioning may be based on existing medical records of a patient, such as clinical imaging records, which are made available to the medical professionals involved with the chemotherapy session.

Once the patient is positioned in the therapeutic magnetic field device, a chemotherapeutic agent is administered (action block 16), marking the beginning of the drug-administration period (action block 14). In certain embodiments, the magnetic field is turned on (action 18) at the same time as the administration of the chemotherapy agent begins, although in alternative embodiments, the magnetic field is turned on at a later time point, as described in greater detail below.

During the drug-administration period, the patient is exposed to a magnetic field having a field strength that is optimal for the chemotherapeutic agent. The duration drug-administration period 14 is dependent on the route of drug-administration, the pharmacokinetics of the chemotherapeutic agent used for treatment, and additional factors as described below. As an example, for infusion chemotherapy, the chemotherapeutic agent can be administered at a pre-determined rate at a pre-determined concentration, hence the chemotherapeutic agent is administered throughout the drug-administration period 14, marked by the start of chemotherapeutic agent administration (action step 16) and the termination of chemotherapeutic agent administration (action step 20) and spanning a duration of T1. The end of chemotherapeutic agent administration (action step 16) typically corresponds to the time point at which the appropriate dosage of the chemotherapeutic agent is administered. However, in cases where the chemotherapeutic agent is administered at a discreet time point (or discreet time points) and not continuously over drug administration period, the end of chemotherapeutic agent administration may instead refer to the time point at which the last dose of the chemotherapeutic agent is administered, or the time point at which the chemotherapeutic agent has reached a pre-defined level of bioavailability.

In the various embodiments, once the patient is exposed to the magnetic field (corresponding to action step 18), magnetic field exposure persists throughout, and continues beyond the drug-administration period 14. The extended period of magnetic exposure ensures that the therapeutic effects of the chemotherapeutic agent, having an appreciable bioavailability after the end of the drug-administration period, are continued to be enhanced by the magnetic field. The total duration of magnetic field exposure T2 is defined as the time between the step of turning on the magnetic field (action step 18) and the step of turning off the magnetic field (action step 22), and hence the extended period of magnetic field exposure T3 is the difference between T2 and T1. T3 is typically equal to 1-5 times the biological half-life (or elimination half-life) of the chemotherapeutic agent. In preferred embodiments, T3 is equal to 3-5 times the biological half-life of the chemotherapeutic agent.

The method disclosed herein is suitable for a number of routes of drug administration. Examples of suitable administration methods include oral administration, intravenous administration, intrathecal administration, and intraperitoneal administration. In preferred embodiments, a chemotherapeutic agent is administered intravenously over a pre-determined duration of time, which is dependent on a number of patient- and drug-specific factors (e.g. patient weight, body surface area, rate of administration, drug concentration . . . etc.) that are well-understood in the art. Magnetic field exposure may begin at the same time as the start of the drug-administration period. Alternatively, commencement of magnetic field exposure may be delayed to a time point where the concentration of the chemotherapeutic agent in blood plasma reaches a suitable value and thereby reduces T2. The length of delay would necessarily depend on the pharmacokinetics of specific chemotherapeutic agents, which determines the bioavailability of the chemotherapeutic agent upon its administration. In some embodiments, magnetic field exposure is delayed for a duration of time equal to the time to maximum concentration ($T_{max}$) of a chemotherapeutic agent, corresponding to the time required for maximum concentration ($C_{max}$) to be reached in blood plasma. In alternative embodiments, magnetic field exposure is delayed for a duration of time more than 50% of the $T_{max}$.

In alternative preferred embodiments, a chemotherapeutic agent is administered orally. Oral administration of chemotherapeutic agents generally occurs at a discreet time point (or several discreet time points), and therefore correspond to a case where the end of the drug administration period corresponds either to the time point at which the last dose of the chemotherapeutic agent is administered, or a pre-determined time point selected in accordance with the pharmacokinetics of the specific chemotherapeutic agent.

For some treatment procedures, a drug cocktail, which comprises a plurality of therapeutic agents, is administered in place of a single chemotherapeutic agent. The drug cocktail comprises a first chemotherapeutic agent, which acts through a free radical intermediate and therefore has a corresponding optimal field strength which enhances its therapeutic effects and has a biological half-life, and further comprises therapeutic agents such as additional chemotherapeutic agents, antibodies, antibody-drug conjugates (ADCs), and cytokines. In certain embodiments, only the first chemotherapeutic agent acts through a free radical mechanism, hence the strength of the magnetic field generated by the therapeutic magnetic field device is set to be equal to the optimal field strength of the first chemotherapeutic agent. After administration of the chemotherapeutic cocktail, the patient is exposed to the magnetic field for a duration of up to 5 times the half-life of the first chemotherapeutic agent.

In alternative embodiments, the drug cocktail comprises a second chemotherapeutic agent which has a shorter biological half-life than the first chemotherapeutic agent, and also acts through a free radical intermediate and therefore has a corresponding optimal field strength which enhances its therapeutic effects. Upon administration of the drug cocktail, the patient is exposed to a magnetic field generated by the therapeutic magnetic field device. The magnetic field may be selected and altered in a number of ways, during and after the drug administration period.

For example, the magnetic field strength can be set to be equal to the optimal field strength of the first chemotherapeutic agent, such that the therapeutic effects of only the first chemotherapeutic agent are enhanced. The magnetic field strength remains the same during over the course of the drug-administration period 14, and also after the drug administration period, for a duration T3 of up to 5 times the biological half-life of the first chemotherapeutic agent.

In alternative embodiments, the magnetic field strength is first set to the optimal field strength of the second chemotherapeutic agent, which has a shorter biological half-life than the first chemotherapeutic and switched to the optimal field strength of the first chemotherapeutic agent at a later time point during the overall treatment procedure. For example, the change in magnetic field strength may occur at a time point up to 5 times the biological life-time of the second chemotherapeutic agent after the end of the drug-administration period 14; for the remainder of the treatment session, the patient is exposed to a magnetic field set to the optimal field strength of the first chemotherapeutic agent. In this example, the total period of magnetic exposure after the drug administration period 14 (T3) is equal to up to 5 times the biological half-life of the first chemotherapeutic agent. While this example only discloses one instance in which the magnetic field strength is changed, it is to be appreciated that the switch in magnetic field strength is informed by knowledge in the pharmacokinetics of each chemotherapeutic agent included in the drug cocktail, and can therefore be adjusted (according to their bioavailability, for example) at any time point during the chemotherapy session, or for a plurality of time points during the chemotherapy session (that is, the magnetic field strength may be switched back-and-forth between values). In different alternative embodiments, the strength of the magnetic field is set to oscillate or alternate between the optimal field strength of the first chemotherapeutic agent and that of the second chemotherapeutic agent.

The methods described herein are applicable to chemotherapeutic agents which act through free radical intermediates. Examples of suitable chemotherapeutic agents include doxorubicin (Adriamycin), oxaliplatin, bleomycin, cycloheximide, vincristine, and other chemotherapeutic agents that act through free radical intermediates.

The various embodiments described herein are suitable for the treatment of cancer tumors of various types. Examples include, but are not limited to bladder cancer, breast cancer, lung cancer, ovarian cancer, thyroid cancer, gastric cancer, bronchogenic cancer, colorectal cancer, testicular cancer, head and neck cancers, cervical cancer, penile and vulval cancers, intracranial germ cell tumors, kidney cancer, rhabdomyosarcoma, neuroblastoma, brain cancer, small cell lung cancer.

For any of the techniques described herein, the magnetic field generated during administration of a chemotherapeutic agent by a therapeutic magnetic field device is between 1-500 gauss. In preferred embodiments, the magnetic field strength is between 1-100 gauss. The optimal field strength is specific to the chemotherapeutic agent. For example, the optimal field strength of doxorubicin has been determined to be 38 gauss. For oxaliplatin, the optimal field strength is 50 gauss.

At least one preferred embodiment makes use of magnetic field shielding devices during the magnetic exposure period. Many chemotherapeutic agents are not target-specific and can affect non-cancerous cells. To prevent the magnetic enhancement of the effects of chemotherapeutic agents in healthy tissue, magnetic shielding is used to cover the non-tumorous sites, leaving only the tumor sites exposed to the magnetic field. The magnetic shielding devices can be provided as portable elements of the therapeutic magnetic field device, or devices that are worn by the patient during treatment. In preferred embodiments, the magnetic shielding devices comprise arrays of ferromagnetic metallic plates. In alternative preferred embodiments, the targeting of specific tissues is enabled by movable source magnets of the therapeutic magnetic field device.

Embodiments of the method disclosed herein will now be described in greater detail by way of the following examples.

Example 1

A 60-year-old black male patient is treated with a combination of doxorubicin and interleukin 2 for unresectable hepatocarcinoma. Staging including clinical imaging studies characterizes the tumor as extensive in the liver with local lymph node involvement.

The initial dose of doxorubicin is administered intravenously at a dose of 60 mg/m² over a 1-hour period on day 1 of a 21-day schedule, which includes interleukin 2. Doxorubicin acts through free radical intermediates and has a biological half-life of 1.5 hours. Animal studies of comparable tumors have identified an optimal magnetic field strength for use in patients receiving doxorubicin to be 38 gauss.

Coincident with the intravenous infusion, the patient is placed in the therapeutic magnetic field device, which controls for anatomical position, patient cardiovascular and respiratory status, and magnetic field parameters to include contour, position and field strength. The patient is positioned on a supportive platform and the conical magnetic field device, which is positioned to the right and left lateral side of the patient with the control station adjacent to the patient. The station integrates prior clinical imaging to assure optimal positioning. The electromagnetic coils are positioned on parallel or axial supports to optimize the field exposure to the hepatic bed and adjacent lymph node sites affected. Hall probes connected to the control station monitor the magnetic field in multiple axes. The patient is comfortably positioned. Magnetic insulating metal plates are positioned to block magnetic field exposure of non-tumorous tissues. The patient is exposed to the magnetic field 38 gauss during the infusion process, and for an additional 4.5 hours after infusion (three times the biological half-life of doxorubicin).

Example 2

A 65-year-old Caucasian female presents with recurrent, locally aggressive rectal adenocarcinoma 10 months following initial surgery. The treatment plan includes radiation therapy and oxaliplatin chemotherapy. Oxaliplatin acts by a known free radical mechanism and has a biological half-life of 25 minutes. The treatment regimen incorporates the intravenous administration of oxaliplatin with a dose of 50 mg/m$^2$ over a period of 2 hours. The drug is to be administered 15 days, 8 days, and 1 day prior to radiation treatment. The tumor recurrence is confined to the rectal area without lymph node involvement. The patient, during the period of oxaliplatin administration, is positioned in the therapeutic magnetic field device with a workstation, which incorporates image controls, which includes prior clinical imaging and patient positioning inputs to assure optimal control of the magnetic field treatment position and contours of the magnetic field. Hall probes directly monitor the magnetic field strength in multiple axes. Magnetic field shielding devices are positioned to prevent exposure of non-tumorous tissue. Prior animal implant studies have identified the optimal field strength for oxaliplatin to be 50 gauss. The patient is treated with a field at 50 gauss throughout the infusion process, and for an additional 75 minutes after infusion (3 times the biological half-life of oxaliplatin).

Also described herein is a therapeutic magnetic field device. A therapeutic magnetic field device comprises a magnetic field generator, a magnetic field sensor, a data entry panel, permitting a user to input time periods and electromagnetic field strengths, for an electromagnetic field production regime, and a data processor including non-transitory computer readable memory, adapted to control said magnetic field generator to output a magnetic field in accordance with data received from said data entry panel.

The magnetic field is generated by magnetic field source such as ferrimagnets and Helmholtz coils. In preferred embodiments, the magnetic field sources are arrayed such that the magnetic field is contoured to fit the topography of irradiated tumor sites. In additional preferred embodiments, the magnetic field sources are moveable and positioned to generate a magnetic field that is contoured to fit the topography of irradiated tumor sites. Magnetic field sensors connected to the control station are used to monitor the magnetic field in multiple axes. In preferred embodiments, the magnetic field sensors are Hall probes.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method for enhancing a chemotherapeutic treatment of cancer tumors in a patient, comprising the steps of:
   (a) placing said patient into a therapeutic magnetic field device comprising
       (i) a magnetic field generator;
       (ii) a magnetic field sensor;
       (iii) a data entry panel, permitting a user to input time periods and electromagnetic field strengths, for an electromagnetic field production regime; and
       (iv) a data processor including non-transitory computer readable memory, adapted to control said magnetic field generator to output a magnetic field in accordance with data received from said data entry panel;
   (b) administering a chemotherapeutic agent, selected from a group including doxorubicin and oxaliplatin, to a patient, said chemotherapeutic agent having a biological half-life and an optimal field strength that is dictated by a specific quantum state of said chemotherapeutic agent;
   (c) during administration of said chemotherapeutic agent, exposing said patient to a magnetic field having said optimal field strength of said chemotherapeutic agent; and
   (d) after administration of said chemotherapeutic agent, exposing the patient to said magnetic field having said optimal field strength of said chemotherapeutic agent for a period up to five-times the biological half-life of said chemotherapeutic agent.

2. The method of claim 1, wherein said chemotherapeutic agent is doxorubicin.

3. The method of claim 1, wherein said cancer tumors comprise rectal cancer tumors.

4. The method of claim 1, wherein said cancer tumors comprise liver cancer tumors.

5. The method of claim 1, wherein said optimal field strength is between 1- 500 gauss.

6. The method of claim 5, wherein said optimal field strength is between 1- 100 gauss.

7. The method of claim 1, wherein the chemotherapeutic agent is administered intravenously.

8. The method of claim 1, wherein the chemotherapeutic agent is administered orally.

9. The method of claim 1, wherein magnetic shielding is used during steps (c) and (d) to prevent magnetic field exposure of non-tumorous tissues.

10. The method of claim 1, wherein said chemotherapeutic agent is oxaliplatin.

* * * * *